United States Patent
Soga et al.

(10) Patent No.: US 10,393,656 B2
(45) Date of Patent: Aug. 27, 2019

(54) OPTICAL INSTRUMENT FOR MEASURING TOTAL REFLECTION ABSORPTION SPECTRUM AND MEASURING DEVICE

(71) Applicant: JASCO CORPORATION, Tokyo (JP)

(72) Inventors: Noriaki Soga, Tokyo (JP); Tetsuji Sunami, Tokyo (JP); Tsubasa Asatsuma, Tokyo (JP); Hiroshi Sugiyama, Tokyo (JP); Jun Koshobu, Tokyo (JP)

(73) Assignee: JASCO CORPORATION, Tokyo (JP)

( * ) Notice: Subject to any disclaimer, the term of this patent is extended or adjusted under 35 U.S.C. 154(b) by 0 days.

(21) Appl. No.: 16/089,146

(22) PCT Filed: Mar. 23, 2017

(86) PCT No.: PCT/JP2017/011608
§ 371 (c)(1),
(2) Date: Sep. 27, 2018

(87) PCT Pub. No.: WO2017/170089
PCT Pub. Date: Oct. 5, 2017

(65) Prior Publication Data
US 2019/0086332 A1    Mar. 21, 2019

(30) Foreign Application Priority Data
Mar. 28, 2016   (JP) ................................. 2016-063294

(51) Int. Cl.
*G01N 21/552*     (2014.01)
*G01N 21/3563*    (2014.01)

(52) U.S. Cl.
CPC ....... *G01N 21/552* (2013.01); *G01N 21/3563* (2013.01)

(58) Field of Classification Search
CPC .. G01N 21/552; G01N 21/532; G01N 33/559; G01N 21/3563
See application file for complete search history.

(56) References Cited

U.S. PATENT DOCUMENTS

| 5,844,682 A | 12/1998 | Kiyomoto et al. |
| 7,978,331 B2 * | 7/2011 | Higashi ............... G01N 21/552 356/301 |

(Continued)

FOREIGN PATENT DOCUMENTS

| JP | H05-10872 A | 1/1993 |
| JP | H7-83824 A | 3/1995 |

(Continued)

OTHER PUBLICATIONS

International Search Report issued in International Bureau of WIPO Patent Application No. PCT/JP2017/011608, dated Jun. 6, 2017.

*Primary Examiner* — David P Porta
*Assistant Examiner* — Fani Boosalis
(74) *Attorney, Agent, or Firm* — Greenblum & Bernstein, P.L.C.

(57) ABSTRACT

An ATR optical instrument condensing an infrared light to a sample-side surface of a ATR crystal to measure a total reflection absorption spectrum includes: an incident-side ellipsoidal mirror condensing the infrared light to the sample-side surface at an incident angle equal to or larger than a critical angle θc inside; an exiting-side ellipsoidal mirror condensing a total reflection light from the sample-side surface; dichroic mirrors guiding an illumination light coaxially to the ellipsoidal mirrors; and a ZnS lens condensing a visible light from the sample-side surface to observe a contact state of the sample. The dichroic mirrors are configured to guide the illumination light to the ellipsoidal mirrors such that the illumination light is condensed to the sample-side surface at an angle less that a critical angle θc'

(Continued)

of the visible light. Accordingly, the ATR optical instrument becomes compact, and can visually observe the contact state of the sample surface.

9 Claims, 5 Drawing Sheets

(56) References Cited

U.S. PATENT DOCUMENTS

| | | |
|---|---|---|
| 2003/0025080 A1 | 2/2003 | Sting et al. |
| 2009/0073436 A1 | 3/2009 | Higashi et al. |

FOREIGN PATENT DOCUMENTS

| | | |
|---|---|---|
| JP | H7-311312 A | 11/1995 |
| JP | 2001-264235 A | 9/2001 |
| JP | 2005/527780 A | 9/2005 |
| WO | 2007/108328 A1 | 9/2007 |

* cited by examiner

OPTICAL INSTRUMENT FOR MEASURING TOTAL REFLECTION ABSORPTION SPECTRUM AND MEASURING DEVICE

RELATED APPLICATIONS

This application claims the priority of Japanese Patent Application No. 2016-063294 filed on Mar. 28, 2016, the disclosure of which is incorporated herein by reference in its entirety.

FIELD OF THE INVENTION

The present invention relates to a measuring device for a total reflection absorption spectrum, and especially to improvement in an optical instrument having an ATR crystal for the measuring device.

BACKGROUND OF THE INVENTION

In a total reflection measuring method (ATR method), when an infrared light is totally reflected at a contact surface between a sample and a prism (also referred to as an ATR crystal), the light enters a surface part of the sample slightly. And the light is absorbed and reflected by the surface part of the sample. The ATR method is a method for measuring an absorption spectrum of the surface part of the sample from its total reflection light. For example, the ATR method is widely used in surface analysis of polymer membranes, semi-conductors, or the like, and analysis of samples that remarkably absorb infrared light such as aqueous solution.

In the ATR method, the sample is placed upside-down on the prism, and the sample and the prism are in a contact state. Therefore, there was a need for grasping which part of the sample is actually being measured in a visible observation image by observing the contact region where total reflection occurs. It is more preferable if a visible observation and a spectrum measurement can be performed simultaneously.

Figure 5:
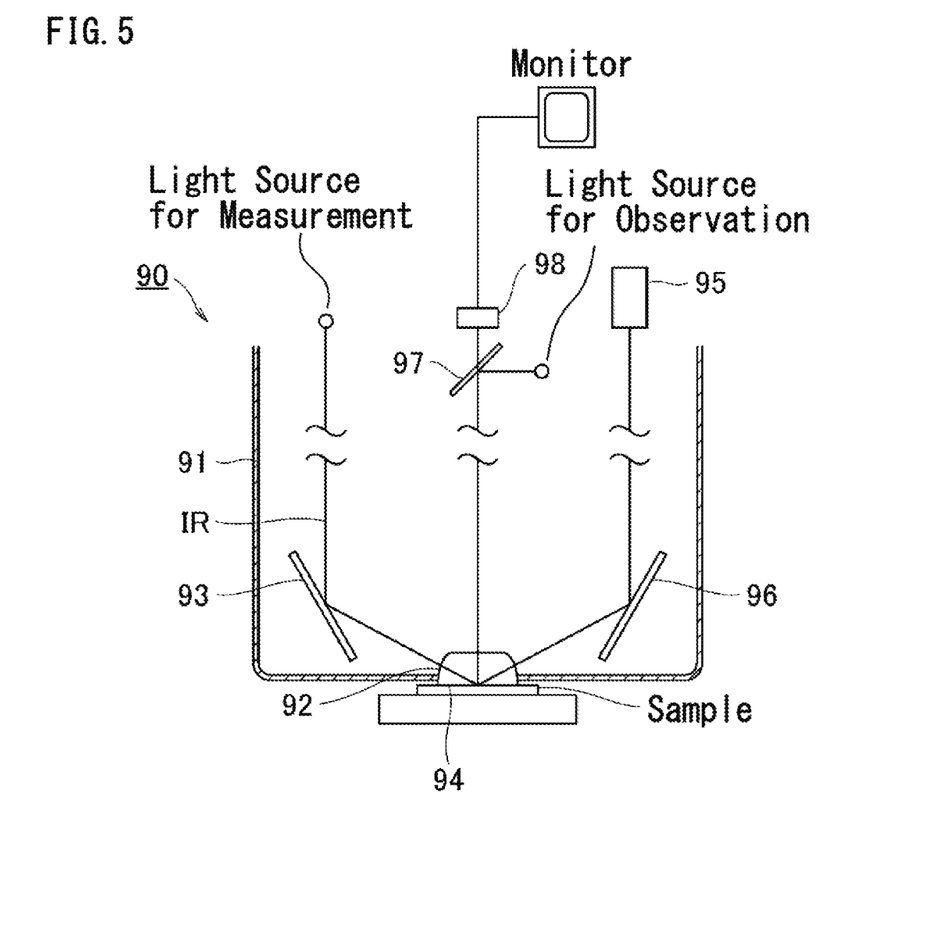
FIG. 5 is a schematic configuration of a conventional ATR prism retaining base.

Patent Literature 1 describes a prism retaining base 90 for the ATR that comprises an optical system for visual observation that uses an infrared light, not a visible light. As shown in FIG. 5, the prism retaining base 90 comprises: a prism 92 that is supported to a housing 91 and transmits an infrared light; a plane mirror 93 that makes an infrared light IR for measuring a spectrum from a light source incident to the prism 92; and a plane mirror 96 that makes a total reflection light exit at a contact surface 94 of the prism to a side of a detector 95 for measuring the spectrum. Further, a half mirror 97 for observing the sample is provided in a direction perpendicular to the contact surface 94 of the prism. FIG. 5 shows a state that the sample on a sample base in contact with the prism 92. In this state, the half mirror 97 reflects the infrared light for observation from the light source for observation to the contact surface 94 of the prism, and transmits a reflected light from the contact surface 94 to an imaging element 98 for observing the sample. That is, the infrared light for observation is irradiated from right above the prism 92 as an illumination light, and the state of the sample is observed by a monitor or the like based on the reflected light from the contact surface 94.

CITATION LIST

Patent Literature

PATENT LITERATURE 1: Japanese Patent Publication No. JPH05-10872

DISCLOSURE OF THE INVENTION

Problem to be Solved by the Invention

Firstly, in a conventional optical configuration for observing the sample of FIG. 5, the half mirror for separating the illumination light and the reflected light must be disposed at a position right above the ATR crystal which has many spatial restrictions. Secondary, most of the illumination light for observation is specularly reflected on the contact surface of the ATR crystal, and the specularly reflected light enters a light receiving element (reference number 98 in FIG. 5). Accordingly, the light receiving element receives information of the contact surface itself, and thus determination of information of the sample to be observed becomes difficult. Further, there are restrictions for the size of the ATR crystal, and it is difficult to make the ATR crystal larger for observing samples.

The present invention has been accomplished in view of the above-mentioned situation, and the aim is to provide an optical instrument and a device for measuring a total reflection absorption spectrum that are configured in a small size and are capable of an accurate visible observation of the contact state of the sample.

Means to Solve the Problem

To achieve the aforementioned aim, an optical instrument for measuring a total reflection absorption spectrum according to the present invention condenses an infrared light on a sample-side surface of an ATR crystal that comes into contact with a sample, and is used to measure an absorption spectrum of a total reflection light from the sample-side surface.

The aforementioned optical instrument comprises:

an ATR crystal having the sample-side surface that comes into contact with the sample;

an infrared light condensing means on an incident side that guides the infrared light to condense at least a portion of the infrared light to the sample-side surface at an incident angle $\theta$ equal to or larger than a critical angle $\theta c$ inside of the ATR crystal;

an infrared light condensing means on an exiting side that condenses the total reflection light from the sample-side surface;

an illumination light guiding means that guides a visible light coaxially to an optical axis of at least one of the infrared light condensing means on the incident side and the exiting side; and a visible light condensing means that condenses the visible light from the sample-side surface to observe a contact state of the sample from a direction different from the respective optical axes of the infrared light condensing means on the incident side and the exiting side, wherein the illumination light guiding means guides the visible light to the infrared light condensing means so that at least a portion of the visible light is condensed to the sample-side surface at an incident angle $\theta'$ less than a critical angle $\theta c'$ of the visible light.

Since the critical angle at the sample-side surface of the ATR crystal depends on a wavelength of light, the critical angle $\theta c$ of the infrared light and the critical angle $\theta c'$ of the visible light are distinguished in the present invention. Further, the optical axis of the infrared light from at least one of the infrared light condensing means and the optical axis of the visible light from the illumination light guiding means are matched. However, a range of the incident angle $\theta$ of the infrared light is not necessarily the same as a range of the incident angle θ' of the visible light. Thus, the references of the incident angles (θ, θ') are distinguished.

Further, it is preferable that the illumination light guiding means guides the visible light to the infrared light condensing means such that the visible light passes almost a half of a cross-section on a side that makes the incident angle θ to the sample-side surface small among a light beam cross-section of the infrared light condensed by the infrared light condensing means. Or, it is preferable that the illumination light guiding means guides the visible light to the infrared light condensing means such that the visible light passes a part of the cross section deviated to the side that makes the incident angle θ' to the sample-side surface small among the light beam cross-section of the infrared light that is condensed by the infrared light condensing means.

Further, it is preferable that the visible light condensing means condenses the visible light along the optical axis perpendicular to the sample-side surface. In this case, the visible light condensing means has a condensing lens for the visible light that is retained independently from the ATR crystal. It is preferable that the condensing lens for the visible light is provided to be in contact with the ATR crystal, has pressure resistance equivalent to the ATR crystal, and is colorless and transparent. Pressure resistance used herein is pressure resistance to pressing force exerted to the ATR crystal when the sample is pressed to the sample-side surface of the ATR crystal.

Further, it is preferable that the infrared light condensing means on the incident side and the exiting side are consisted of ellipsoidal mirrors. Further, it is preferable that the illumination light guiding means forms the optical axis of the visible light connected to the optical axis of the infrared light condensing means, and is provided with a mask that blocks a part of the light beam cross-section of the visible light on the optical axis of the visible light. Further, it is preferable that the illumination light guiding means has a splitting optical configuration of the visible light that splits the visible light from one illumination light source to guide one to the infrared light condensing means on the incident side, and the other to the infrared light condensing means on the exiting side.

Further, to achieve the aforementioned aim, the measuring device for a total reflection absorption spectrum according to the present invention condenses at least a part of an infrared light on a sample-side surface of an ATR crystal that comes into contact with a sample at an incident angle θ equal to or larger than a critical angle θc of the infrared light to measure an absorption spectrum of a total reflection light from the sample-side surface.

The aforementioned measuring device comprises: an ATR crystal having a sample-side surface that comes into contact with a sample;

an infrared light emitting means that emits an infrared light;

an infrared light condensing means on an incident side that guides the infrared light from the infrared light emitting means to condense the infrared light at an incident angle θ equal to or larger than a critical angle θc inside the ATR crystal;

an infrared light condensing means on an exiting side that condenses a total reflection light from the sample-side surface;

a light detecting means that detects the total reflection light from the infrared light condensing means;

an illumination light guiding means that guides a visible light coaxially to an optical axis of at least one of the infrared light condensing means on the incident side and the exiting side; and a visible light condensing means that condenses the visible light from the sample-side surface to observe a contact state of the sample from a direction different from the respective optical axes of the infrared light condensing means on the incident side and the exiting side, wherein the illumination light guiding means guides the visible light to the infrared light condensing means so that at least a part of the visible light is condensed to the sample-side surface at an incident angle θ' less than a critical angle θc' of the visible light.

Effect of the Invention

According to the optical instrument and the measuring device of the present invention that are configured as described above;

(1) the illumination light guiding means guides the visible light for observation to the infrared light condensing means "coaxially" to the optical axis of the infrared light for measurement or of its total reflection light. The visible light for observation, the illumination light, condensed coaxially to the optical axis of this infrared light is made incident obliquely to the sample-side surface at an angle equal to or larger than a prescribed angle. Therefore, the illumination light that specularly reflects on the sample-side surface of the ATR crystal does not enter an optical path for observation that is in a direction, for example, perpendicular to the sample-side surface of the ATR crystal. Since the specularly reflected light of illumination conventionally caused illumination unevenness, the present invention can suppress illumination unevenness caused by the specularly reflected light of illumination.

Moreover, the infrared light condensing means condenses at least a part of the illumination light to the sample-side surface at the incident angle θ' that is "less than the critical angle θc' of the visible light" by the illumination light guiding means, so that the all of the illumination light is not totally reflected on the sample-side surface. That is, at least a part of the illumination light is refracted at the sample-side surface and proceeds to the sample side. Then, the visible light condensing means collects a diffused reflection light that contains information of the sample itself, so that the contact information of the sample can be observed for sure.

The present invention utilizes that the refractive index of the visible light is larger than that of the infrared light, and a condition for total reflection at the sample-side surface depends on a wavelength of the incident light. Further, the optical axes of the illumination light consisted of the visible light and the infrared light are matched, and they are made incident at a condition such that not all of the illumination light totally reflect on the sample-side surface. The infrared light condensing means forms beam-spots of the infrared light and the illumination light at a same position on the sample-side surface. Therefore, even if the infrared light and the illumination light are coaxial, at least a part of the illumination light can be made incident to the ATR crystal at an angle that the light is not totally reflected by using the optical axis of the infrared light as stated above by setting the light beam cross-section of the illumination light to a suitable shape, or suitably adjusting the shape of the cross-section. Further, in both of the infrared light condensing means on the incident side and the exiting side, an observing field can be illuminated uniformly by providing the illumination light guiding means that guides the illumination light coaxially.

(2) The illumination light for observation is guided to the infrared light condensing means "coaxially" to the optical axis of the infrared light or its total reflection light. Therefore, an optical path dedicated for irradiating the illumination light to the ATR crystal does not need to be formed, and thus the ATR crystal and the optical system can be made compact.

(3) As one embodiment of the present invention, the optical axis of the visible light for observation from the sample-side surface is formed perpendicularly to the sample-side surface of the ATR crystal, and a condensing lens (for example, ZnS) for the visible light is provided on this optical axis. The illumination light for observation and the infrared light for measurement are coaxial, and the illumination light guiding means of an oblique irradiation type is provided. Therefore, a condensing lens suitable for condensing light from the ATR crystal can be used as the condensing lens for the visible light. That is, the condensing lens has pressure resistance equivalent to the ATR crystal and is colorless and transparent, and is supported in contact with the ATR crystal. Therefore, it can be configured as a lens integrated with the ATR crystal and can achieve a wide visual field range and high color reproducibility.

Pressure resistance as used herein is pressure resistance with respect to pressing force exerted to the ATR crystal when the sample is pressed to the sample-side surface of the ATR crystal. When the condensing lens is soft, the ATR crystal bites into the condensing lens for the visible light by pressing force generated when the sample is made into contact with the ATR crystal. Since the present invention uses the condensing lens having pressure resistance equivalent to that of the ATR crystal, such problems of pressure resistance can be prevented. Hence, a clear observation image can be obtained even if the ATR crystal is made into contact with the sample by pressing force.

According to the present invention, the optical instrument for measuring the total reflection absorption spectrum that includes the ATR crystal can be configured in a compact size, the contact part and its contact state of the sample can be observed for sure, and reliability of measurement can be improved. Similarly, the measuring device for measuring the total reflection absorption spectrum can be configured in a compact size, and the contact part and its contact state of the sample can be observed for sure.

DESCRIPTION OF REFERENCE NUMBERS

2 Observing camera
4, 104 Diamond prism (ATR crystal)
6, 106 Sample-side surface
8 Infrared light incident surface
10 ATR optical instrument (optical instrument for measuring a total reflection absorption spectrum)
12 Infrared light exiting surface
14 Visible light exiting surface
16, 26 Plane mirror
18, 24 Dichroic mirror (illumination light guiding means)
20, 22 Ellipsoidal mirror (infrared light condensing means)
28, 34 Illuminating LED
30, 36 Collimating lens
32, 38 Mask
40 ZnS lens (visible light condensing means)
42, 44 A pair of lenses (visible light condensing means)
50 Sample base
52 Infrared light source (infrared light emitting means)
54 Interferometer (infrared light emitting means)
56, 58 Condensing lens
60 Light detector
62 Signal processor
100 Measuring device for a total reflection absorption spectrum
120, 122 Condensing lens (infrared light condensing means)
S Sample
IR Infrared light
TR Total reflection light
L1, L2 illumination light
θc Critical angle of the infrared light
θc' Critical angle of the visible light

BEST MODE FOR CARRYING OUT THE INVENTION

Hereinbelow, preferable embodiments of the present invention are described with reference to the figures.

First Embodiment

Figure 1:
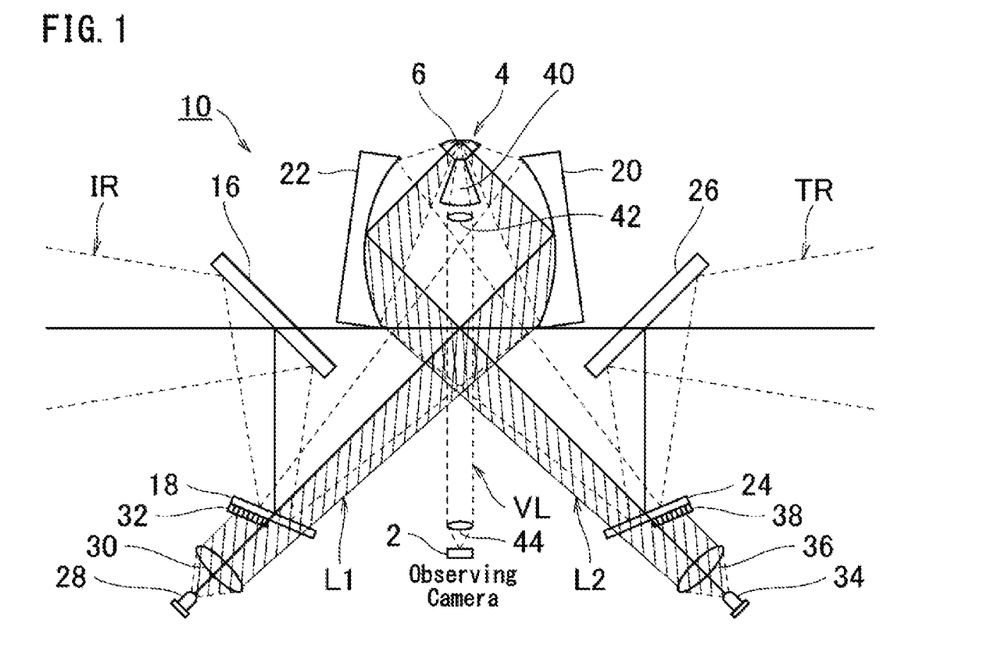
FIG. 1 is a schematic configuration of an ATR optical instrument according to a first embodiment.
Figure 2:
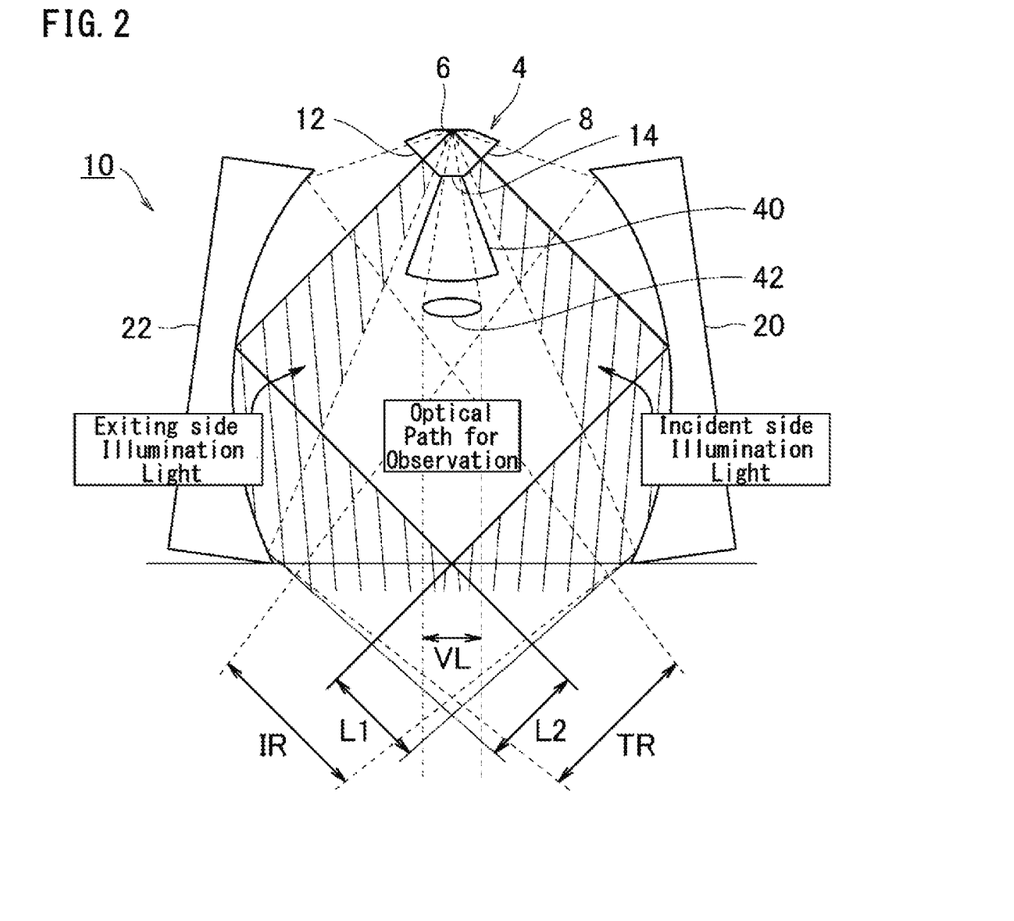
FIG. 2 is an enlarged view of a main part of the ATR optical instrument.

FIG. 1 shows a schematic configuration of an ATR optical instrument 10 according to a first embodiment of an optical instrument of the present invention. FIG. 2 shows an enlarged view of a main part of the ATR optical instrument 10. The ATR optical instrument 10 is disposed in a sample chamber or the like of a Fourier-transform infrared spectrophotometer (FTIR), for example. It is an accessory for exhibiting an ATR function, and supports a diamond prism, a mirror or a lens for forming an optical path of the infrared light to a housing to configure a prescribed optical system.

As shown in FIGS. 1 and 2, in the ATR optical instrument 10, an optical axis of an optical system for observation of a visible light from a sample to an observing camera 2 is formed in a direction perpendicular to a sample-side surface 6 of a prism 4. An incident optical system of an infrared light and an exiting optical system of a total reflection light are formed symmetrically having this optical axis of the optical system for observation as a center.

<Diamond Prism as the ATR Crystal>

A diamond prism 4 is retained to a housing (not shown) so that the sample-side surface 6 of the prism is exposed to a sample side at an upper part of the figure. The prism 4 has: the sample-side surface 6 that comes into contact with the sample as shown in FIG. 2; an infrared light incident surface 8 and an infrared light exiting surface 12 that form prescribed angles with the sample-side surface 6; and a visible light exiting surface 14 parallel to the sample-side surface 6. To the infrared light incident surface 8, an infrared light is made incident from the outside at an angle that the infrared light totally reflects on the sample-side surface 6 (an angle equal to or larger than a critical angle θc of the infrared light). In FIG. 2, the optical system is adjusted such that the optical axis of the infrared light crosses the infrared light incident surface 8 perpendicularly and the infrared light is made incident to the sample-side surface 6 at the critical angle θc. Simultaneously, an illumination light from a first direction is made incident coaxially to the optical axis of the infrared light.

In this embodiment, not all of the infrared light need to be at the incident angle equal to or larger than the critical angle θc, and the infrared light can be made incident to the sample-side surface 6 at an angle that a part of the infrared light is not totally reflected.

The infrared light exiting surface 12 makes a total reflection light of the infrared light from the sample-side surface 6 exit to the outside, and receives irradiation of the illumination light from a second direction that are coaxial to the optical axis of the infrared light. The visible light exiting surface 14 makes the visible light that contains information of the contact state of the sample exit to a direction perpendicular to the sample-side surface 6.

The prism 4 is not limited to diamonds, and it can be of any material that has high transparency to the visible light and the infrared light. For example, ZnS (Zinc sulphide) or KRS-5 (Thallium bromoiodide) may be used. Further, if color information of the sample need not to be accurate, KRS-5 (Thallium bromoiodide) or ZnSe (Zinc selenide) that transmit only the long wavelength side of the visible light and are colored.

As for the shape of the ATR crystal, a semi-spherical shaped crystal of which the infrared light incident surface 8, the infrared light exiting surface 12 and the visible light exiting surface are formed on a common semi-spherical surface may be used. Further, the ATR crystal of single-reflection type is given as an example in the present embodiment, but ATR crystals of multiple-reflection type, such as double-reflection, can be applied to the present invention.

<Ellipsoidal Mirror as the Infrared Light Condensing Means on the Incident Side>

An incident optical system of the infrared light is provided to condense the infrared light supplied from the external infrared light source to the prism 4, and comprises: a plane mirror 16 that reflects an infrared light IR guided from the left hand side in the Figure; a dichroic mirror 18 that reflects the infrared light from the plane mirror 16; and an ellipsoidal mirror 20 that reflects the infrared light from the dichroic mirror 18.

A mirror surface of the dichroic mirror 18 is disposed at one focal position of the ellipsoidal mirror 20, and the sample-side surface 6 of the prism is disposed at another focal position of the ellipsoidal mirror 20. In the present embodiment, the infrared light IR from the infrared light source side is condensed to the dichroic mirror 18, and is condensed to the sample-side surface 6 at low magnification by the ellipsoidal mirror 20. The ellipsoidal mirror 20 configures the optical instrument 10 for a so-called macro measurement together with an ellipsoidal mirror 22 on the exiting side, which will be described later. For example, when the ellipsoidal mirrors 20, 22 of a magnification of about 4 are used, beam-spots of about one-quarter of beam-spots formed on the mirror surfaces of the dichroic mirrors 18, 24 are formed on the sample-side surface 6.

The mirror surface of the ellipsoidal mirror 20 on the incident side is formed axially symmetrical to the mirror surface of the ellipsoidal mirror 22 on the exiting side, which will be described later, having the optical axis of the optical system for observation as a center, and they are disposed to face each other. In the present embodiment, two of the ellipsoidal mirrors 20, 22 on the incident side and the exiting side are disposed around the optical axis of the optical system for observation, but an ellipsoidal mirror that goes round the optical axis for observation may be used, too.

<Ellipsoidal Mirror as the Infrared Light Condensing Means on the Exiting Side>

On the other hand, an exiting optical system of the total reflection light comprises an ellipsoidal mirror 22, a dichroic mirror 24 and a plane mirror 26 that are disposed symmetrically to the aforementioned incident optical system having the optical axis of the optical system for observation as a center. That is, the sample-side surface 6 is disposed at one focal position of the ellipsoidal mirror 22 on the exiting side, and a mirror surface of a dichroic mirror 24 on the exiting side is disposed at another focal position of the ellipsoidal mirror 22 on the exiting side. The ellipsoidal mirror 22 on the exiting side condenses a total reflection light TR of the infrared light from the sample-side surface 6 and reflects the total reflection light towards the dichroic mirror 24 on the exiting side. The dichroic mirror 24 reflects the total reflection light from the ellipsoidal mirror 22 to a plane mirror 26 on the exiting side. The plane mirror 26 reflects the total reflection light from the dichroic mirror 24 to a light detector disposed on the right hand side of the Figure. Accordingly, the exiting optical system makes the total reflection light from the prism 4 exit to the light detector disposed outside.

With respect to the infrared light IR supplied from the light source side, an infrared light of a dispersing type spectrophotometer may be used, but an interference wave of the infrared light by a double-beam interferometer such as an FTIR is preferable.

Now, an illumination system on the incident side and the exiting side and the optical system for observation for observing the contact state of the sample that are the characteristic features of the present invention are described.

<Dichroic Mirror as an Illumination Light Guiding Means>

The aforementioned dichroic mirrors 18, 24 that configure the incident optical system and the exiting optical system can reflect the infrared light, transmit the visible light, and acts as the illumination light guiding means of the present invention. An illumination system on the incident side consisted of an LED light source 28 and a collimating lens 30 is formed on an extended line of the optical axis of the infrared light from the dichroic mirror 18 to the ellipsoidal mirror 20 on the incident side. An illumination light L1 from the LED light source 28, shown with hatchings of parallel lines in the Figure, is collimated approximately into a parallel light beam by the collimating lens 30, transmits through the dichroic mirror 18, is reflected on the ellipsoidal mirror 20, and is condensed to the sample-side surface 6 of the prism. By the dichroic mirror 18, the illumination light L1 consisted of the visible light joins coaxially to the optical axis of the infrared light IR to the ellipsoidal mirror 20 on the incident side. A prism-shaped one may be used as the dichroic mirror 18, and a polarizing beam splitter may be used instead.

A mask 32 that blocks a part of the light beam cross-section of the illumination light L1 is provided to a surface on the LED light source side of the dichroic mirror 18. A region that is covered by the mask 32 is set so that at least a part of the illumination light L1 is condensed to the sample-side surface 6 at the incident angle θ' less than the critical angle θc' of the visible light when the illumination light L1 that passed through the part where it is not covered by the mask 32 is condensed to the sample-side surface 6 by the ellipsoidal mirror 20. In FIGS. 1 and 2, the region of the mask 32 is set such that the illumination light L1 passes through almost the half of the cross-section on a side that makes the incident angle θ' to the sample-side surface small among the light beam cross-section of the infrared light IR condensed by the ellipsoidal mirror 20. Or, the region of the mask 32 may be set such that the illumination light L1 passes through a part of the cross-section deviated to a side that makes the incident angle θ' to the sample-side surface 6 small among the light beam cross-section of the infrared light IR condensed by the ellipsoidal mirror 20.

Similarly, an illumination system on the exiting side supplies an illumination light L2 to the ellipsoidal mirror 22 on the exiting side coaxially to the optical axis of the total reflection light TR. That is, similar to the incident side, the illumination system on the exiting side consisted of an LED light source 34 and a collimating lens 36 is formed on an extended line of the optical axis of the total reflection light TR from the ellipsoidal mirror 22 to the dichroic mirror 24 on the exiting side. Further, a mask 38 that blocks a part of the light beam cross-section of the illumination light L2 is provided to a surface on the LED light source side of the dichroic mirror 24.

The masks 32, 38 are not limited to those provided to the surfaces of the dichroic mirrors 18, 24, but may be light blocking plates disposed on optical paths between the dichroic mirrors 18, 24 and the collimating lens 30, 36. Further, a visible light filter that transmits the infrared light and blocks the visible light may be stuck to the surfaces on the ellipsoidal mirrors 20, 22 sides of the dichroic mirrors 18, 24, or disposed on the optical paths between the dichroic mirrors 18, 24 and the ellipsoidal mirrors 20, 22.

<Optical System for Observation>

An optical system for observation to observe the contact state of the sample is consisted of: a zinc sulphide (ZnS) lens 40 for condensing a visible light exited from the visible light exiting surface 14 of the diamond prism 4; a pair of lenses 42, 44 that collimates a visible light VL condensed by the ZnS lens 40 into a parallel light to guide it to a direction perpendicular to the sample-side surface 6; and an observing camera 2 for imaging the visible light VL guided by the pair of lenses 42, 44.

In the present embodiment, the ZnS lens 40 and the pair of lenses 42, 44 correspond to a visible light condensing means of the present invention, and the ZnS lens 40 corresponds to a condensing lens for the visible light of the present invention. The optical system for observation consisted of the ZnS lens 40, the pair of lenses 42, 44, and the observing camera 2 forms an optical path of the visible light VL perpendicularly to the sample-side surface 6, and condenses/guides/images the visible light VL along the optical path. The ZnS lens 40 is retained to the housing independently from the prism 4. Further, the lens 40 is provided to be in contact with the prism 4, has pressure resistance equivalent to that of the diamond prism 4, and is colorless and transparent. The shape of the ZnS lens 40 shown in FIG. 2 is merely an example. In this example, the lens 40 has a contact surface with the visible light exiting surface 14 of the prism 4 at an upper part, a convex surface at a lower part, and a conical shaped body part having a point on the sample-side surface as its apex. That is, the shape of the lens 40 is determined in such a manner that it does not overlap with the optical paths of the infrared light IR and the total reflection light TR guided by the ellipsoidal mirrors 20, 22, and a wide range of the sample part can be condensed. By such optical system for observation, the light from the sample in contact with the sample-side surface 6 is condensed by the prism 4 and the ZnS lens 40, further guided to the pair of lenses 42, 44, and made incident to the observing camera 2. The diamond prism 4 and the ZnS lens 40 have near refractive indices, and a combination thereof can be uses as one lens. When a zinc selenide (ZnSe) lens is used as the condensing lens as a comparative example, it lacks color information as an observing image because the crystal is yellow. Further, it has a problem of pressure resistance when it is made into contact with the sample because it is softer than the diamond prism 4. Observation is possible without the ZnS lens 40, but the combination of the diamond prism 4 and the ZnS lens 40 can achieve configuration of the optical system for observation that has a wider visual field range and is excellent in color reproducibility and pressure resistance. The condensing lens is not limited to the ZnS lens 40, but can be of any other material that has pressure resistance equivalent to the ATR crystal and is colorless and transparent. Colorless and transparent high-refractive glasses having a refractive index of 1.8 or higher such as a sapphire glass, L-BBH1 manufactured by OHARA Inc., or K-PSFn214 manufactured by Sumita Optical Glass, Inc. may be used.

<Measuring Device for a Total Reflection Absorption Spectrum>

Figure 3:
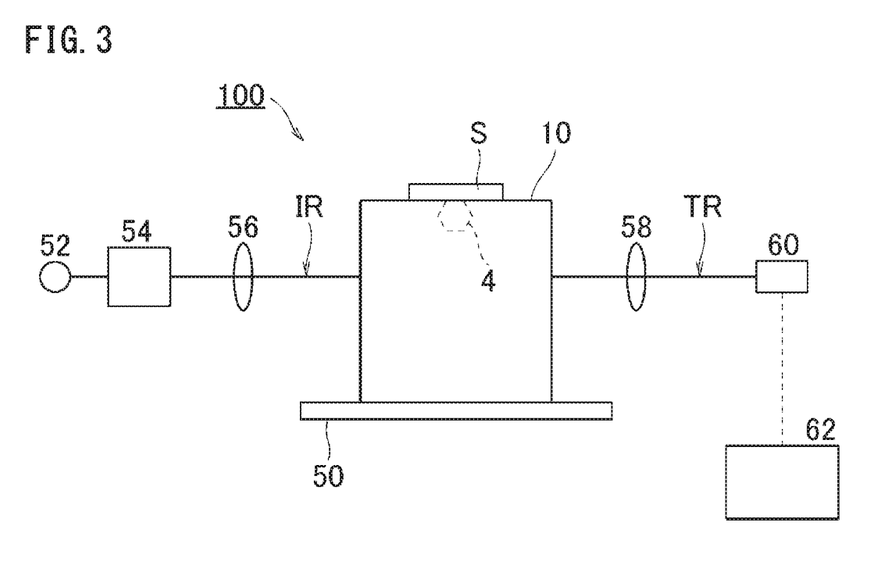
FIG. 3 is a schematic configuration of a total reflection measuring device that includes the ATR optical instrument.

FIG. 3 shows a schematic configuration of a measuring device 100 for a total reflection absorption spectrum that uses the ATR optical instrument 10 of the present embodiment. The measuring device 100 for the total reflection absorption spectrum is based on an FTIR or a dispersing type spectrophotometer, and is configured by combining with the aforementioned optical instrument 10. In the example of FIG. 3, the ATR optical instrument 10 is disposed on a sample base 50 (or a sample chamber) at a center part of the measuring device 100. The infrared light IR for measurement is supplied from the incident optical system to the optical instrument 10, and the total reflection light TR from the optical instrument 10 is guided to the exiting optical system. The incident optical system of the infrared light comprises an infrared light source 52, an interferometer 54 and a condensing lens 56, and condenses an interference wave of the infrared light IR from the interferometer 54 to supply it to the optical instrument 10 in a horizontal direction. A part of the interference wave of the infrared light IR is absorbed by a surface part of the sample S that comes into contact with the diamond prism 4 of the ATR optical instrument 10, and the remaining part of the infrared light exits from the optical instrument 10 as the total reflection light TR. The exiting optical system of the total reflection light TR comprises a condensing lens 58, a light detector 60 and a signal processor 62, and detects the total reflection light TR exited from the optical instrument 10 in the horizontal direction to calculate a spectrum data by a Fourier-transform process.

<Effect of the Present Embodiment>

(1) The dichroic mirror 18 on the incident side guides the illumination light L1 to the ellipsoidal mirror 20 coaxially to the infrared light IR for measurement, so that the illumination light that is specularly reflected on the sample-side surface 6 does not enter the optical path for observation, and illumination unevenness can be suppressed. Moreover, the ellipsoidal mirror 20 condenses the illumination light L1 to the sample-side surface 6 of the prism at the incident angle less than the critical angle θc' of the visible light, so that total reflection of the illumination light L1 at the sample-side surface 6 can be suppressed, too. Accordingly, the illumination light L1 is refracted at the sample-side surface 6 of the prism, proceeds to the sample side, and is diffused and reflected at the sample S. Irradiation of the illumination light L2 by the dichroic mirror 24 and the ellipsoidal mirror 22 on the exiting side is similar to that of the incident side. A light from the sample S generated by the illumination lights L1, L2, is condensed by the diamond prism 4 and the ZnS lens 40, so that a diffused and reflected light having information of the contact state of the sample S can be observed.

The effect of the present embodiment can be obtained if at least a part of the illumination lights L1, L2 is made incident at the incident angle less than the critical angle $\theta c'$. Therefore, it is not necessary that all of the illumination lights L1, L2 are made incident at the incident angle less than the critical angle $\theta c'$.

(2) In both of the ellipsoidal mirrors 20, 22 on the incident side and the exiting side, the dichroic mirrors 18, 24 respectively guide the illumination lights L1, L2 coaxially, so that the visual field for observation can be uniformly illuminated.

(3) The illumination lights L1, L2 for observation are guided to the ellipsoidal mirrors 20, 22 coaxially to the optical axis of the infrared light IR or its total reflection light TR. Therefore, an optical path dedicated to irradiate the illumination light to the diamond prism 4 does not to have be formed, and thus the prism 4 and the optical system can be made compact.

(4) The ZnS lens 40 suitable for condensing the visible light VL from the prism 4 can be provided on the optical axis of the optical system for observation. That is, the ZnS 40 that has pressure resistance equivalent to that of the diamond prism 4, is colorless and transparent, and has the equivalent refractive index is used to be in contact with and support the prism 4, so that it can be configured as a lens integrated with the prism 4, and can achieve a wide visual field range and high color reproducibility.

(5) By setting the light beam cross-sections of the illumination lights L1, L2 to suitable shapes and suitably adjusting the shapes of the cross-sections by using the masks 32, 38, the illumination lights L1, L2 can be made incident to the diamond prism 4 at an angle that the light is not totally reflected even if they are coaxial to the optical axis of the infrared light IR.

Second Embodiment

Figure 4:
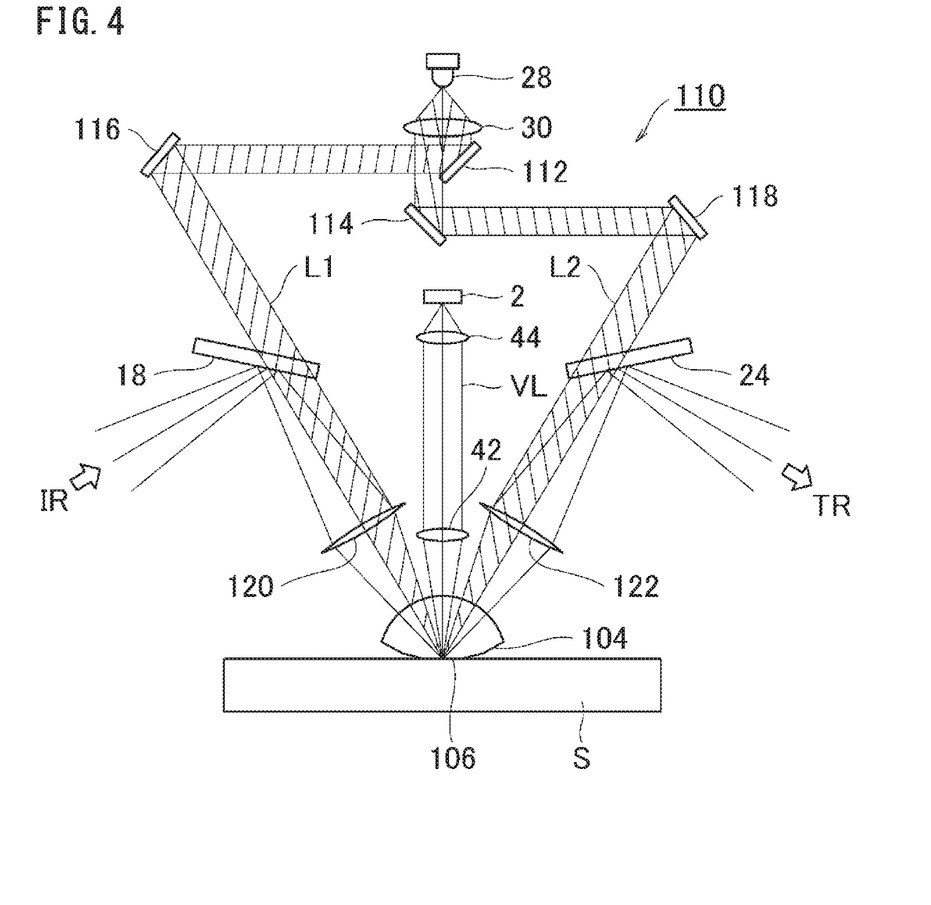
FIG. 4 is a schematic configuration of the ATR optical instrument according to a second embodiment.

FIG. 4 shows a schematic configuration of an ATR optical instrument 110 of a second embodiment. Elements in common with the first embodiment are numbered with the same reference numbers, and only the configurations different from the first embodiment will be described below.

In the ATR optical instrument 110 of the present embodiment, an ATR prism 104 is retained so that a sample-side surface 106 faces downward, and the prism 104 is disposed to be in contact with an upper surface part of the sample S. Further, instead of the ellipsoidal mirror of the first embodiment, the infrared light IR from the dichroic mirror 18 on the incident side is condensed to the sample-side surface 106 of the prism by a condensing lens 120 on the incident side, and the total reflection light TR from the sample-side surface 106 is condensed to the dichroic mirror 24 on the exiting side by a condensing lens 122 on the exiting side. The visible light for observation from the sample-side surface 106 is condensed by the prism 104 and the pair of lenses 42, 44, and is made incident to the observing camera 2.

The second embodiment does not use the ellipsoidal mirror. It has a splitting optical configuration of the visible light that splits a half of the visible light from one LED illumination 28 by a mirror (mask) 112 to guide it to the dichroic mirror 18 on the incident side via a mirror 116, and guides the remaining half of the visible light to the dichroic mirror 24 on the exiting side via the mirrors 114, 118.

As for disposition of the ellipsoidal mirror as the infrared light condensing means, when the viewing the prism 4 from the sample side in the first embodiment, the ellipsoidal mirrors 20, 22 are disposed in two positions to face each other around the prism 4, but they may be disposed in three or more positions around the prism 4. For example, if four ellipsoidal mirrors are to be disposed at every 45° around the prism, the ellipsoidal mirrors for incidence of the infrared light and for exit of the total reflection light are alternately disposed. In such disposition of the four ellipsoidal mirrors, the dichroic mirror for coaxial irradiation of the illumination light is preferably provided to at least one of the four ellipsoidal mirrors.

Further, the optical axis of the optical system for observation is formed perpendicularly to the sample-side surface 6 of the prism, but it does not have to be perpendicular and can be in an oblique angle to the sample-side surface 6. However, it is preferable to form the optical axis perpendicularly like the present embodiment because distortion of the sample portion in an observing image can be smaller.

What is claimed is:

1. An optical instrument for measuring a total reflection absorption spectrum condensing an infrared light on a sample-side surface of an ATR crystal that comes into contact with a sample, and being used to measure an absorption spectrum of a total reflection light from the sample-side surface, comprising:
   an ATR crystal having the sample-side surface that comes into contact with the sample;
   an infrared light condensing means on an incident side that guides the infrared light to condense at least a portion of the infrared light to the sample-side surface at an incident angle equal to or larger than a critical angle $\theta c$ inside of the ATR crystal;
   an infrared light condensing means on an exiting side that condenses the total reflection light from the sample-side surface;
   an illumination light guiding means that guides a visible light coaxially to an optical axis of at least one of the infrared light condensing means on the incident side and the exiting side; and
   a visible light condensing means that condenses the visible light from the sample-side surface to observe a contact state of the sample from a direction different from the respective optical axes of the infrared light condensing means on the incident side and the exiting side,
   wherein the illumination light guiding means guides the visible light to the infrared light condensing means so that at least a portion of the visible light is condensed to the sample-side surface at an incident angle less than a critical angle $\theta c'$ of the visible light.

2. The optical instrument according to claim 1, wherein the illumination light guiding means guides the visible light to the infrared light condensing means such that the visible light passes almost a half of a cross-section on a side that makes the incident angle to the sample-side surface small among a light beam cross-section of the infrared light condensed by the infrared light condensing means.

3. The optical instrument according to claim 1, wherein the visible light condensing means condenses the visible light along the optical axis perpendicular to the sample-side surface.

4. The optical instrument according to claim 3, wherein the visible light condensing means has a condensing lens for the visible light that is retained independently from the ATR crystal,
the condensing lens for the visible light is provided to be in contact with the ATR crystal, has pressure resistance equivalent to the ATR crystal, and is colorless and transparent.

5. The optical instrument according to claim 1, wherein the infrared light condensing means on the incident side and the exiting side are consisted of ellipsoidal mirrors.

6. The optical instrument according to claim 1, wherein the illumination light guiding means forms the optical axis of the visible light connected to the optical axis of the infrared light condensing means, and is provided with a mask that blocks a part of the light beam cross-section of the visible light on the optical axis of the visible light.

7. The optical instrument according to claim 1, wherein the illumination light guiding means has a splitting optical configuration of the visible light that splits the visible light from one illumination light source to guide one split beam to the infrared light condensing means on the incident side, and the other split beam to the infrared light condensing means on the exiting side.

8. The optical instrument according to claim 1, wherein the illumination light guiding means
guides the visible light to the infrared light condensing means such that the visible light passes almost a half of a cross-section on a side that makes the incident angle to the sample-side surface small among a light beam cross-section of the infrared light condensed by the infrared light condensing means,
forms the optical axis of the visible light connected to the optical axis of the infrared light condensing means, and
is provided with a mask that blocks a part of the light beam cross-section of the visible light on the optical axis of the visible light, and
the visible light condensing means condenses the visible light along the optical axis perpendicular to the sample-side surface.

9. A measuring device for a total reflection absorption spectrum condensing at least a part of an infrared light on a sample-side surface of an ATR crystal that comes into contact with a sample at an incident angle equal to or larger than a critical angle $\theta c$ of the infrared light to measure an absorption spectrum of a total reflection light from the sample-side surface, comprising:
an ATR crystal having a sample-side surface that comes into contact with a sample;
an infrared light emitting means that emits an infrared light;
an infrared light condensing means on an incident side that guides the infrared light from the infrared light emitting means to condense the infrared light at an incident angle equal to or larger than a critical angle $\theta c$ inside the ATR crystal;
an infrared light condensing means on an exiting side that condenses a total reflection light from the sample-side surface;
a light detecting means that detects the total reflection light from the infrared light condensing means;
an illumination light guiding means that guides a visible light coaxially to an optical axis of at least one of the infrared light condensing means on the incident side and the exiting side; and
a visible light condensing means that condenses the visible light from the sample-side surface to observe a contact state of the sample from a direction different from the respective optical axes of the infrared light condensing means on the incident side and the exiting side,
wherein the illumination light guiding means guides the visible light to the infrared light condensing means so that at least a part of the visible light is condensed to the sample-side surface at an incident angle less than a critical angle $\theta c'$ of the visible light.

* * * * *